United States Patent [19]

Deckner

[11] Patent Number: 4,781,914
[45] Date of Patent: Nov. 1, 1988

[54] SUNSCREEN AND MOISTURIZER

[75] Inventor: George E. Deckner, Westfield, N.J.

[73] Assignee: Charles of the Ritz Group Ltd., New York, N.Y.

[21] Appl. No.: 804,564

[22] Filed: Dec. 4, 1985

[51] Int. Cl.[4] .......................... A61K 7/42; A61K 7/44; A61K 7/48; A61K 9/10

[52] U.S. Cl. ........................................ 424/59; 424/47; 424/60; 514/847; 514/873; 514/938; 514/940; 514/943

[58] Field of Search ..................... 514/938, 940, 943; 424/59, 60, 47

[56] References Cited

U.S. PATENT DOCUMENTS

| | | | |
|---|---|---|---|
| 4,216,201 | 8/1980 | Calvo | 424/63 |
| 4,254,104 | 3/1981 | Suzuki | 519/938 |
| 4,350,605 | 9/1982 | Hughett | 424/45 |
| 4,454,113 | 6/1984 | Hemker | 514/938 |
| 4,522,808 | 6/1985 | Jacquet et al. | 424/81 |

OTHER PUBLICATIONS

"CTFA Cosmetic Ingredient Dictionary", Third Edition, p. 244.

*Primary Examiner*—Dale R. Ore
*Attorney, Agent, or Firm*—Lerner, David, Littenberg, Krumholz & Mentlik

[57] ABSTRACT

Skin treatment compositions such as sun screen compositions and moisturizer compositions are provided which include polyglyceryl-8 oleate to impart moisture resistance or substantivity to the compositions.

11 Claims, No Drawings

SUNSCREEN AND MOISTURIZER

FIELD OF THE INVENTION

The present invention relates to improved skin treatment compositions, such as sunscreen compositions and moisturizer compositions which are in the form of oil-in-water emulsions, also referred to as creamy-oils, but upon being rubbed into the skin invert to water-in-oil emulsions having improved substantivity.

BACKGROUND OF THE INVENTION

Ultraviolet energy absorbed by the human skin can produce an erythemal reaction (redness), the intensity of which is dependent upon the amount of energy absorbed. Ultraviolet radiation from both sunlight and artificial sources has been divided into three bands (UV-A, UV-B, and UV-C) which emit different quantities of energy and therefore produce an erythemal reaction at different time intervals after exposure. The amount of energy from any source required to produce a minimally perceptible redness reaction of the skin is termed the Minimal Erythema Dose or MED.

UV-A radiation is present in the sunlight reaching the earth's surface and has a wavelength of 320 to 400 nanometers (nm.). It can cause tanning of the skin but is weak in causing reddening of the skin. About 20 to about 50 joules/cm$^2$ of UV-A energy is required to produce one MED. The erythema reaction is maximal in intensity about 24 hours after exposure.

UV-B radiation is present in the sunlight reaching the earth's surface and has a wavelength of 290 to 320 nm. It causes the sunburn reaction which also stimulates pigmentation (tanning) in the skin. Approximately 20 to 50 millijoules/cm$^2$ of UV-B energy is required to produce one MED (i.e., about 1,000 times less than the dose of UV-A). The erythema reaction is maximal in intensity at from about 6 to about 20 hours after exposure.

UV-C radiation has a wavelength of 200 to 290 nm. and is not present in the sunlight reaching the earth's surface but can be emitted by artificial ultraviolet sources. It is not effective in stimulating pigmentation but does cause erythema requiring about 5 to 20 millijoules/cm$^2$ to produce one MED.

The tanning ability of an individual is genetically predetermined and is governed by the individual's capacity to produce melanin pigment within the pigment cells when stimulated by UV-B and UV-A. The extent of any erythemal response is a function of skin color and thus less time is required to produce a MED in light skinned individuals than to produce a MED in dark skinned individuals.

The most rapid way to cause tanning is to allow the sun to produce erythema of the skin. Erythema sufficient to induce tanning yet not so severe as to cause pain requires only half the time of exposure that is required to produce a painful sunburn. Suntanning can occur at the UV-A wavelengths but develops slowly under natural conditions. Tanning most commonly develops after exposure to the "sunburn" UV-B band.

Sunscreen preparations are commercially available which extend the time it takes the sun to produce a sunburn. Such preparations contain chemicals which can absorb ultraviolet light at various wavelengths, for example, 4-(dimethylamino)benzoic acid, 2-ethylhexyl ester (Escalol 507) and 2-hydroxy-4-methoxybenzophenone (UVinul M40) which absorb UV-A, or an opaque substance that physically reflects or scatters the ultraviolet light, i.e. talc.

Ultraviolet absorbing compounds and sunscreen compositions containing the same are disclosed, for example, in U.S. Pat. No. 3,004,896; 3,189,615; 3,403,207; 3,479,428; 3,644,614; 3,670,074; 3,751,563; 3,821,363; 3,892,844; 4,514,383; and British Pat. No. 1,291,917.

Commercially available sun screen and sun block formulations provide excellent protection against severe sun burning of exposed skin for extended periods so long as they remain on exposed areas and are not washed off by bathing. Unfortunately, bathing in pool water and ocean water will usually result in most conventional sun screen and sun block formulations being washed away from the skin thereby leaving exposed areas of skin. Attempts have been made at formulating sun screen products which are moisture resistant. For example, see U.S. Pat. No. 3,666,732.

Accordingly, effective sun screen and sun block formulations which remain on the skin even after bathing, that is, are water-resistant, for extended periods of time would indeed fulfill a long-felt want.

DESCRIPTION OF THE INVENTION

In accordance with the present invention, moisture resistant skin treatment compositions, such as sun screen and sun block formulations, and moisturizer formulations are provided, which compositions have improved moisture resistance and substantivity due to the presence therein of polyglyceryl-8 oleate and are in the form of oil-in-water emulsions which contain in addition to polyglyceryl-8 oleate, water, emollients, and humectants. Optional ingredients which may be included are thickeners, preservatives, coloring agents, fragrances, antioxidants and the like. In the case of sun screen or sun block formulations, the compositions of the invention will include one or more known ultraviolet absorbing compounds. In fact, the moisturizer compositions of the invention will be similar in composition to the sun screen or sun block formulations except for the presence or absence of the ultraviolet absorbing compound.

The compositions of the invention, in the form of cream-oils, are unique in that they are initially formulated as thin sprayable oil-in-water emulsions which are easily spreadable when rubbed onto the skin and impart a pleasant cooling effect. However, in rubbing, water evaporates (due to heat and shear forces) and the oil-in-water emulsion inverts to a water-in-oil emulsion which has a creamy feel similar to an oil but which is not greasy to the touch and leaves a substantive film on the skin surface. Thus, in essence, the formulation is applied as an oil-in-water emulsion, which has relatively poor substantivity and is normally easily washed away by water, and then upon rubbing water evaporates (due to heat generated from the skin) and the oil-in-water emulsion inverts to a water-in-oil emulsion (referred to as a cream-oil), which has excellent substantivity and imparts a creamy non-greasy feel to the skin.

Depending upon the choice of ingredients, the formulation has a semi-solid thin cream-oil-like consistency which can be packaged in a spray container, or in a plastic squeeze tube or container.

The container can include a flow-type cap or pump-type non-aerosol dispenser to effect spraying. However, the container may also be of the aerosol type.

The essence of the present invention resides in the use of polyglyceryl-8 oleate to effect emulsification of the ingredients to form the oil-in-water emulsions of the invention and to enhance moisture resistance. Polyglyceryl-8 oleate is an ester of oleic acid and a glycerin polymer containing an average of 8 glyceryl units, a commercially available form thereof being known as Santone 8-1-0 (Durkee Foods). Thus, the composition of the invention, regardless of whether it is a sun screen, sun block, moisturizer, etc. will contain from about 0.5 to about 10% and preferably about 2 to about 7% by weight (based on the total weight of the formulation) of polyglyceryl-8 oleate. Where amounts less than 0.5% by weight polyglyceryl-8 oleate are employed, emulsification will be incomplete so that the formulation will be too unstable and thus unacceptable, whereas, where amounts greater than 10% by weight are employed, the formulation will be too stable and not capable of inverting to a water-in-oil on the skin.

Where the formulation is a sun screen or sun block formulation, it will contain one or more known ultraviolet absorbing agents, preferably at least one compound which absorbs in the UV-B region (wavelength 290 to 320 nanometers) and at least one compound which absorbs in the UV-A region (wavelength 320 to 400 nanometers). The total amount of UV absorbing agents included within the formulation will be from about 3% to about 15% by weight, which amount will determine whether it is a sun screen or sun block.

Suitably UV-A absorbing agents include 2-(2'-hydroxy-5'-methylphenyl)benzotriazole (Tinuvin P); 2-(2'-hydroxy-5'-t-octylphenyl)benzotriazole (Spectra-Sorb UV 5411); 2,4-dihydroxybenzophenone (Uvinul 400); 2-hydroxy-4-methoxybenzophenone (oxybenzone, Spectra-Sorb UV9, Uvinul M-40); 2,2',4,4'-tetrahydroxybenzophenone (Uvinul D50); 2,2'-dihydroxy-4,4'-dimethoxybenzophenone (Uvinul D49); 2,2'-dihydroxy-4-methoxybenzophenone (dioxybenzone, Spectra-Sorb UV24); 2-ethylhexyl-4-phenyl-benzophenone carbonate (Eusolex 3573); 2-hydroxy-4-methoxy-4'-methylbenzophenone (mexenone, Uvistat 2211); 2-hydroxy-4-(n-octyloxy)benzophenone (octabenzone, SpectraSorb UV531); 4-phenylbenzophenone (Eusolex 3490); and 2-ethylhexyl-2-cyano-3,3'-diphenylacrylate (Uvinul N539). The UV-A absorbing agent or agents are present in the final product at from about 0.5% to about 10% by weight of the formulation. The amount will vary according to the particular agent selected and whether the formulation is intended to minimize or permit tanning. The preferred UV-A absorbing agent is 2-hydroxy-4-methoxybenzophenone alone or in combination with 2,2'-dihydroxy-4-methoxybenzophenone.

Suitable UV-B absorbing agents include 4-(dimethylamino)benzoic acid, ethyl ester; 4-(dimethylamino)benzoic acid, 2-ethylhexyl ester (Escalol 507); 4-(dimethylamino)benzoic acid, pentyl ester (Escalol 506); glyceryl p-aminobenzoate (Escalol 106); isobutyl p-aminobenzoate (Cycloform); and isopropyl p-aminobenzoate. The UV-B absorbing agent or agents are present in the final product at from about 1% to about 15% by weight of the formulation. The amount will vary according to the particular agent selected and degree of protection desired in the final product. The preferred UV-B absorbing agent is 4-(dimethylamino)benzoic acid, 2-ethylhexyl ester.

The formulation also contains from about 50% to about 90% and preferably from about 60 to about 80% by weight of water, from about 1% to about 35% and preferably from about 5 to about 25% by weight of emollients, from about 1% to about 10% and preferably from about 1 to about 5% by weight of humectants, usually in the form of polyols, from about 0.05 to about 2% and preferably from about 0.1 to about 1% by weight of preservatives and antioxidants, and less than about 2% by weight of fragrance and coloring agents.

Suitable emollients include mineral oil, lanolin alcohol, cyclomethicone, avocado oil, squalane, octyl palmitate, cocoa butter, sesame oil, petrolatum, propylene glycol dicaprylate/dicaprate, isopropyl myristate, etc. The formulation will preferably cotain a mixture of several of these emollients or others which are approved for cosmetic use.

Examples of polyols (which will also serve as humectants) suitable for use herein inlcude, but are not limited to glycerin, propylene glycol, 1,3-butylene glycol, sorbitol, polyethylene glycol (for example, PEG 8), sorbitol, glycerin, polyoxyethylene (26) glyceryl ether (Liponic EG1), propylene glycol, 1,3-butylene glycol or hexylene glycol with polyoxyethylene (26) glyceryl ether being preferred.

Suitable preservatives include propylene glycol, imidazolidinyl urea (Germall 115), diazodinyl urea, methylparaben (Tegosept M), quaternium-15 (N-(3-chloroallyl)hexaminium chloride, Dowcil 200), propylparaben (Tegosept P), dimethyldimethoyl hydantoin, benzyl alcohol and/or phenoxyethanol, etc., and the preferred antioxidant is a mixture of butylated hydroxyanisole, propylene glycol, propyl gallate and citric acid (Tenox 2). The formulation will preferably contain one or more of the above preservatives or any other preservatives and optimally antioxidants approved for cosmetic use.

The composition of the invention will optionally include a thickener in an amount within the range of from about 0.05 to about 1% and preferably from about 0.05 to about 0.3% by weight. A preferred thickener suitable for use herein is Carbopol 940 or Carbomer 940 which is hydrophilic acrylic polymer cross-linked with a polyfunctional agent and employed with an organic or inorganic base, preferably triethanolamine. Other examples of thickeners which may be employed herein include, but are not limited to, stearic acid, magnesium aluminum silicate, stearoxydimethicone, hydroxyethyl cellulose, hydroxypropyl cellulose or xanthan gum.

Skin conditioning agents which may optionally be present in the composition of the invention include allantoin, d- or dl-panthenol, hydrolyzed animal protein and the like. Such conditioning agents may be present in an amount within the range of from about 0.01 to about 5% and preferably from about 0.05 to about 2% by weight and from about 0.1 to about 20% by weight depending upon the ultimate use of the skin preparation.

The cream-oils of the invention may also be in the form of an aerosol spray and as such are formulated with any conventional hydrocarbon propellant or other acceptable propellants. The hydrocarbon propellant, when employed, will be present in an amount within the range of from about 5 to about 15% by weight and preferably from about 7.5 to about 12.5% by weight of the total composition. A preferred hydrocarbon propellant is a mixture of isobutane and propane. Other examples of hydrocarbon propellants suitable for use herein include butane, propane, dimethyl ether, Freon 12 or Freon 114.

The process techniques will vary depending upon the particular ingredients present. In a preferred process, a mixture of water, humectant such as glycerin, polyglyceryl-8 oleate emulsifier and preservative, such as methylparaben, propyl paraben, propylene glycol and diazodinyl urea are heated to form an aqueous blend. A mixture of sun screen agents (where present), emollients, such as mineral oil, lanolin alcohol and cyclomethicone, are blended together to form a non-aqueous blend. Each of the blends are heated to a temperature within the range of from about 45° to about 60° C.

Thereafter the non-aqueous blend is added to the aqueous blend in a mill and the mixture is milled and then subjected to sweep mixing to form the oil-in-water emulsion of the invention.

Preferred sun block formulations offering maximum protection according to this invention include from about 60% to about 80% by weight of water, from about 1% to about 5% by weight of polyglyceryl-8 oleate, from about 2.5% to about 3.5% by weight of UV-A absorbing agents selected from 2-hydroxy-4-methoxybenzophenone (oxybenzone) and 2,2'-dihydroxy-4-methoxybenzophenone (dioxybenzone), from about 3% to about 7% by weight of the UV-B absorbing agent 4-(dimethylamino)benzoic acid, 2-ethylhexyl ester (Escalol 507), from about 2 to about 8% by weight of humectants, from about 5% to about 30% by weight of emollients, from about 0 to about 0.5% by weight thickeners, up to about 1% by weight of combined preservatives, and up to about 2% by weight of fragrances.

Most preferably the maximum protection formulation will contain from about 65 to about 72% by weight of deionized water, from 2 to about 4% by weight of polyglyceryl-8 oleate, from about 1.5 to about 3% by weight of 2-hydroxy-4-methoxybenzophenone, up to about 1% by weight of 2,2'-dihydroxy-4-methoxybenzophenone, from about 3.5 to about 8% by weight of 4-(dimethylamino)benzoic acid, 2-ethylhexyl ester, from about 10% to about 25% by weight of emollients, about 5% by weight of emulsifiers, and up to 1.5% by weight of combined preservatives, and fragrances.

Preferred sunscreen formulations which protect but still permit gradual tanning according to this invention contain from about 65% to about 75% by weight of water, from about 1 to about 5% by weight of polyglyceryl-8 oleate, up to about 1% by weight of 2-hydroxy-4-methoxybenzophenone (oxybenzone), from about 1% to about 5% by weight of 4-(dimethylamino)benzoic acid, 2-ethylhexylester (Escalol 507), up to about 7.5% by weight of humectants, from about 15 to about 25% by weight of emollients, and up to about 15% by weight of combined preservatives and fragrances.

The most preferred sunscreen formulation which still permits tanning is a lotion containing from about 65% to about 75% by weight of deionized water, about 3% by weight of a polyglyceryl-8 oleate, about 0.6% by weight of 2-hydroxy-4-methoxybenzophenone, about 4% by weight of 4-(dimethylamino)benzoic acid, 2-ethylhexyl ester, about 5% by weight of glycerin or propylene glycol, from about 15% to about 25% by weight of emollients, and up to about 1.5% by weight of combined preservatives and fragrances.

Preferred moisturizer compositions will be similar to the sunscreen and sun block formulations set out above without the sunscreen agents.

It will be appreciated that the term "moisturizer compositions" as employed herein refers to sprayable thin oil-in-water skin moisturizer compositions such as sprayable face, hands and body moisuturizers.

The following Examples represent preferred embodiments of the invention. Unless otherwise indicated, all temperatures are expressed in degrees Centigrade.

EXAMPLE 1

A sprayable sunscreen formulation in the form of an oil-in-water emulsion having a sun protection factor value of 4 having the following composition was prepared as described below. The ingredients are listed on a parts by weight basis. The SPF value is determined by dividing minimal erythema dose (MED) for protected skin after the application of 2 mg/cm$^2$ of the formulation by the MED for unprotected skin.

| Ingredient | Parts by Weight |
|---|---|
| Blend A | |
| Deionized water | 67 |
| Glycerine (humectant) | 5 |
| Polyglyceryl-8 oleate (emulsifier) | 3 |
| Pre blend of | |
| 40% Propylene glycol  20% Methylparaben  10% Propylparaben and  30% Diazodinyl urea } Preservative | 0.5 |
| Blend B | |
| 4-(Dimethylamino)benzoic acid, 2-ethylhexyl ester (Escalol 507, sun screen, UV-B) | 4 |
| Cyclomethicone (emollient) | 10 |
| Mineral oil and lanolin alcohol (1:1, emollient) | 10 |
| Perfume oil | 0.4 |

Aqueous Blend A was prepared by dispersing all Blend A ingredients in the deionized water and heating to 50° C. Blend B (prepared by simple mixing of ingredients and heating to 50° C.) was then mixed with Blend A on a mill. The combined Blend A-B was milled for 15 minutes and then was mixed by sweep mixing at 35° C.

The resulting batch was then allowed to air cool to 30° C. to form the oil-in-water sun screen formulation of the invention.

Upon application and rubbing on the skin, the oil-in-water sun screen formulation of the invention inverted to a water-in-oil emulsion, which had a creamy but non-greasy feel, and produced a moisturizing film which had excellent substantivity which was resistant to water and perspiration, but was removable by washing with soap.

EXAMPLE 2

A cream-oil moisturizing body spray in accordance with the present invention having the following composiion was prepared as described below.

The ingredients are listed on a parts by weight basis.

| Ingredient | Parts by Weight |
|---|---|
| Blend A | |
| Deionized water | 71 |
| Polyglyceryl-8 oleate (emulsifier) | 3 |
| Glycerine (humectant) | 5 |
| Pre blend of | |
| 40% Propylene glycol  20% Methylparaben  10% Propylparaben  30% Diazodinyl urea } Preservative | 0.5 |

-continued

| Ingredient | Parts by Weight |
| --- | --- |
| Blend B | |
| Cyclomethicone (emollient) | 10 |
| Mineral oil and lanolin alcohol (1:1) (emollient) | 10 |
| Perfume oil | 1 |

Aqueous Blend A was prepared by dispersing all Blend A ingredients in the deionized water and heating at 50° C. Blend B (prepared by simple mixing of ingredients and heating to 50° C.) was then mixed with Blend A on a mill. The combined Blend A-B was milled for 15 minutes and then was sweep mixed at 35° C. for 30 minutes. The resulting batch was then air-dried to form the sprayable oil-in-water moisturizer of the invention. Upon applying to the skin and rubbing the oil-in-water moixturizer inverted to a water-in-oil formulation which had a creamy non-greasy feel and excellent substantivity.

The water-in-oil emulsion produced a moisturizing film having excellent substantivity and was resistant to water and perspiration but was removable by washing with soap.

What is claimed is:

1. A moisture-resistant skin treatment composition in the form of a sprayable oil-in-water emulsion, comprising water, at least one emollient, polyglyceryl-8 oleate as an emulsifier in an amount within the range of from about 0.5 to about 10% by weight based on the total composition to impart moisture-resistance to said composition, which upon being applied to the skin and rubbed thereon inverts to a water-in-oil creamy, non-greasy film having excellent substantivity.

2. The composition as defined in claim 1 wherein said polyglyceryl-8 oleate is present in an amount within the range of from about 2 to about 7% by weight.

3. The composition as defined in claim 1 in the form of a moisture-resistant sun screen composition and includes from about 1 to about 15% by weight of at least one ultraviolet absorbing agent.

4. The composition as defined in claim 1 wherein the ultraviolet absorbing agents include one or more UV-A absorbing and one or more UV-B absorbing agents.

5. The composition as defined in claim 4 wherein the UV-A absorbing agent or agents are present at from about 0.5% to about 10% by weight and the UV-B absorbing agent or agents are present at from about 3% to about 10% by weight.

6. The composition as defined in claim 5 wherein the UV-A absorbing agent is one or more selected from the group consisting of 2-(2'-hydroxy-5'-methylphenyl)benzotriazole; 2-(2'-hydroxy-5'-t-octylphenyl)benzotriazole; 2,4-dihydroxybenzophenone; 2-hydroxy-4-methoxybenzophenone; 2,2',4,4'-tetrahydroxybenzophenone; 2,2'-dihydroxy-4,4'-dimethoxybenzophenone; 2,2'-dihydroxy-4-methoxybenzophenone; 2-ethylhexyl-4-phenylbenzophenone carbonate; 2-hydroxy-4-methoxy-4'-methylbenzophenone; 2-hydroxy-4-(n-octyloxy)benzophenone; 4-phenylbenzophenone; and 2-ethylhexyl-2-cyano-3,3'-diphenylacrylate and the UV-B absorbing agent is one or more selected from the group consisting of 4-(dimethylamino)benzoic acid, ethyl ester; 4-(dimethylamino)benzoic acid, 2-ethylhexyl ester; 4-(dimethylamino)benzoic acid, pentyl ester; glyceryl p-aminobenzoate; isobutyl p-aminobenzoate; and isopropyl p-aminobenzoate.

7. The composition as defined in claim 5 wherein the UV-A absorbing agent is 2-hydroxy-4-methoxybenzophenone alone or in combination with 2,2'-dihydroxy-4-methoxybenzophenone and the UV-B absorbing agent is 4-(dimethylamino)benzoic acid, 2-ethylhexyl ester.

8. The composition as defined in claim 1 wherein water is present in an amount of from about 50 to about 90% by weight, emollients are present in an amount of from about 1 to about 35% by weight, humectants are present in an amount of from about 1 to about 10% by weight, preservatives are present in an amount of from about 0.1 to about 1% by weight.

9. The composition as defined in claim 3 offering maximum ultraviolet protection and moisture resistance comprising from about 60% to about 80% by weight of water, from about 2% to about 7% by weight of polyglyceryl-8 oleate, from about 1% to about 5% by weight of 2-hydroxy-4methoxybenzophenone alone or in combination with 2,2'-dihydroxy-4-methoxybenzophenone, from about 3% to about 10% by weight of 4-(dimethylamino)benzoic acid, 2-ethylhexyl ester, from about 5% to about 25% by weight of emollients, and up to about 2% by weight of combined preservatives and fragrances.

10. The method of enhancing the moisture resistant properties of a sun screen composition which contains water, one or more ultraviolet absorbing agents, emollient, humectants and which comprises including from about 0.5 to about 10% by weight of polyglyceryl-8 oleate in the composition.

11. The method as defined in claim 10 wherein the sun screen composition contains from about 3% to about 15% by weight of ultraviolet absorbing agents and the polyglyceryl-8 oleate is included at from about 2 to about 7% by weight of the composition.

* * * * *